United States Patent
Ohuchi et al.

(10) Patent No.: US 10,368,821 B2
(45) Date of Patent: Aug. 6, 2019

(54) IMAGE PROCESSING APPARATUS, MEDICAL IMAGE DIAGNOSTIC APPARATUS AND IMAGE PROCESSING METHOD

(71) Applicant: Canon Medical Systems Corporation, Otawara-Shi (JP)

(72) Inventors: Hiroyuki Ohuchi, Otawara (JP); Shinichi Hashimoto, Otawara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 1044 days.

(21) Appl. No.: 14/797,364

(22) Filed: Jul. 13, 2015

(65) Prior Publication Data
US 2016/0015349 A1    Jan. 21, 2016

(30) Foreign Application Priority Data

Jul. 16, 2014 (JP) .................. 2014-145846

(51) Int. Cl.
| | | |
|---|---|---|
| *A61B 5/00* | (2006.01) | |
| *A61B 6/00* | (2006.01) | |
| *A61B 6/03* | (2006.01) | |
| *A61B 8/08* | (2006.01) | |

(52) U.S. Cl.
CPC .......... *A61B 6/5229* (2013.01); *A61B 5/0035* (2013.01); *A61B 5/0042* (2013.01); *A61B 5/0044* (2013.01); *A61B 5/489* (2013.01); *A61B 5/7425* (2013.01); *A61B 6/032* (2013.01); *A61B 6/5217* (2013.01); *A61B 8/483* (2013.01);

(Continued)

(58) Field of Classification Search
CPC ..... A61B 6/5229; A61B 6/032; A61B 6/5217; A61B 8/483; A61B 5/7425; A61B 5/0042; A61B 5/0044; A61B 5/489; A61B 5/0035; A61B 8/5261; A61B 2576/00; A61B 6/501; A61B 6/503
See application file for complete search history.

(56) References Cited

U.S. PATENT DOCUMENTS 6,426,990 B1 * 7/2002 Cesmeli ................ A61B 6/504
378/4
8,340,374 B2 * 12/2012 Yamagata .............. A61B 6/032
382/100
(Continued)

FOREIGN PATENT DOCUMENTS

| JP | 2009-106530 | 5/2009 |
|---|---|---|
| JP | 2009-160235 | 7/2009 |
| JP | 2012-81254 | 4/2012 |

OTHER PUBLICATIONS

Japanese Office Action dated Apr. 2, 2019 in Japanese Application No. 2015-138293, 3 pages.

*Primary Examiner* — Brenda C Bernardi
(74) *Attorney, Agent, or Firm* — Oblon, McClelland, Maier & Neustadt, L.L.P.

(57) ABSTRACT

The image processing apparatus includes a processing circuitry. The processing circuitry is configured to obtain first volume data showing a morphological shape of an object and second volume data showing information corresponding to a position spatially different from a position of the object. The processing circuitry is configured to provide the information in the second volume data to the position of the object in the first volume data.

20 Claims, 14 Drawing Sheets

3D IMAGE BASED ON 3RD VOLUME DATA

(52) U.S. Cl.
CPC ............ *A61B 8/5261* (2013.01); *A61B 6/501* (2013.01); *A61B 6/503* (2013.01); *A61B 2576/00* (2013.01)

(56) References Cited

U.S. PATENT DOCUMENTS

| | | | | |
|---|---|---|---|---|
| 8,560,050 | B2 * | 10/2013 | Martin | A61B 5/055 |
| | | | | 382/128 |
| 8,605,964 | B2 * | 12/2013 | Fichtinger | G06T 7/33 |
| | | | | 382/128 |
| 9,891,784 | B2 * | 2/2018 | Lee | A61B 8/466 |
| 2009/0326363 | A1 * | 12/2009 | Li | A61B 8/12 |
| | | | | 600/411 |
| 2011/0263964 | A1 * | 10/2011 | Bernhardt | A61B 5/02014 |
| | | | | 600/407 |
| 2012/0101368 | A1 * | 4/2012 | Masumoto | A61B 6/503 |
| | | | | 600/420 |
| 2012/0165674 | A1 * | 6/2012 | Abe | A61B 8/0883 |
| | | | | 600/443 |
| 2014/0321726 | A1 * | 10/2014 | Shin | A61B 8/5261 |
| | | | | 382/131 |
| 2015/0257845 | A1 * | 9/2015 | Gopalakrishna | A61B 6/503 |
| | | | | 600/424 |
| 2015/0297161 | A1 * | 10/2015 | Grass | A61B 6/503 |
| | | | | 600/426 |

* cited by examiner

3D IMAGE BASED ON CORONARY ARTERY VOLUME DATA

3D IMAGE BASED ON CARDIAC FUNCTION VOLUME DATA

3D IMAGE BASED ON 3RD VOLUME DATA

IMAGE PROCESSING APPARATUS, MEDICAL IMAGE DIAGNOSTIC APPARATUS AND IMAGE PROCESSING METHOD

CROSS-REFERENCE TO RELATED APPLICATION

This application is based upon and claims the benefit of priority from Japanese Patent Application No. 2014-145846, filed on Jul. 16, 2014, the entire contents of which are incorporated herein by reference.

Further, the contents of Japanese Patent Application No. 2015-138293, filed on Jul. 10, 2015, which claims priority to Japanese Patent Application No. 2014-145846 are also incorporated herein by reference in their entirety.

FIELD

An embodiment of the present invention relates to an image processing apparatus, a medical image diagnostic apparatus and an image processing method for generating a diagnostic image.

BACKGROUND

An X-ray computed tomography (CT) apparatus generates imaging CT volume data through an imaging method, as three-dimensional (3D) data including cardiovascular morphological information. An image processing apparatus extracts coronary artery volume data encompassing a coronary artery on the basis of the imaging CT volume data, and displays the coronary artery volume data as a 3D image. Such display allows an operator to visually identify a narrowing portion of a cardiac coronary artery.

An ultrasonic diagnostic apparatus generates multi-frame 3D data (cardiac wall volume data) including morphological information on cardiac walls (endocardial, myocardial and epicardial walls). The image processing apparatus analyzes the multi-frame cardiac wall volume data, and calculates cardiac function information (wall movement information), thereby generating cardiac function volume data mapped according to the degree of cardiac function information and displaying the cardiac function volume data as a 3D image. Such display enables the degree of cardiac function information to be quantified.

An image processing apparatus has also been known that aligns coronary artery volume data with cardiac function volume data, combines both the data items, and displays the combined data. The image processing apparatus aligns the coronary artery volume data with the cardiac function volume data, then combines both the data items to generate combined volume data, and displays the generated data as a 3D image. An operator can easily grasp the positional relationship between a vascular narrowing portion indicated in the coronary artery volume data and a cardiac malfunctioning portion indicated by the cardiac function volume data on the basis of the displayed 3D image. Consequently, the displayed 3D image of the combined volume data is effective in determining necessity of treatment and identifying a portion to be treated.

Moreover, an image processing apparatus has been disclosed that generates combined volume data showing the relationship between a vascular narrowing portion based on coronary artery volume data and cardiac malfunctioning portion (cardiac wall movement abnormal portion) based on cardiac function volume data, and displays the generated data as a multi-planar reconstruction (MPR) image.

The conventional image processing apparatus for displaying the combined volume data showing the relationship between the vascular narrowing portion and the cardiac malfunctioning portion can present the operator with the distance between the cardiac malfunctioning portion and the coronary artery, where the cardiac malfunctioning portion has a strain value, or cardiac function information, higher than a threshold. However, this apparatus cannot present the operator with the strain value itself. Furthermore, the determination as to whether a portion is a cardiac malfunctioning portion or not depends on the threshold of strain value that is for identifying a cardiac malfunctioning portion. Accordingly, the distance between the cardiac malfunctioning portion and the coronary artery varies depending on the threshold. Consequently, it is difficult to set a single threshold, which would otherwise be appropriate for the conventional image processing apparatus.

The operator has to search for a close part of the blood vessel where a Strain level has decreased, the close part being close to a part of the blood vessel where a diagnosis or a treatment is necessary, so as to identify the diagnosis or treatment part. In other words, there is a problem that cannot decide a blood vessel responsible for the cardiac malfunctioning portion.

In the conventional technique that aligns the coronary artery volume data with the cardiac function volume data and then generates combined volume data, the 3D image is displayed in such a manner that a vascular narrowing portion is hidden behind a cardiac malfunctioning portion displayed at the front in the direction of line of sight of the 3D image. Consequently, the operator cannot visually identify the vascular narrowing portion behind. In order to allow the operator to visually identify the vascular narrowing portion behind and thus exhaustively identify the vascular narrowing portion and the cardiac malfunctioning portion, the operator is required to repeat a turning operation (an operation of turning the direction of line of sight) for the displayed 3D image. This operation becomes burden on the operator.

BRIEF DESCRIPTION OF THE DRAWINGS

In accompanying drawings.

DETAILED DESCRIPTION

An image processing apparatus, a medical image diagnostic apparatus and an image processing method according to the present embodiments are described with reference to the accompanying drawings.

To solve the above-described problems, the present embodiment provides the image processing apparatus, including a processing circuitry configured to obtain first volume data showing a morphological shape of an object and second volume data showing information corresponding to a position spatially different from a position of the object, and to provide the information in the second volume data to the position of the object in the first volume data.

To solve the above-described problems, the present embodiment provides the medical image diagnostic apparatus, including: a scanner taking an image of an object to generate one of first volume data showing a morphological shape of the object and second volume data showing a position spatially different from a position of the object; and a processing circuitry, wherein the processing circuitry is configured to obtain other data between the first volume data and the second volume data, and to provide the information in the second volume data to a position of the object in the first volume data.

To solve the above-described problems, the present embodiment provides the image processing method, including: obtaining first volume data and second volume data from a storage, the first volume data showing a morphological shape of an object, the second volume data showing information corresponding to a position spatially different from a position of the object; providing the information in the second volume data to the position of the object in the first volume data to generate a third volume data; and displaying the third volume data as an image to a display.

First Embodiment

Figure 1:
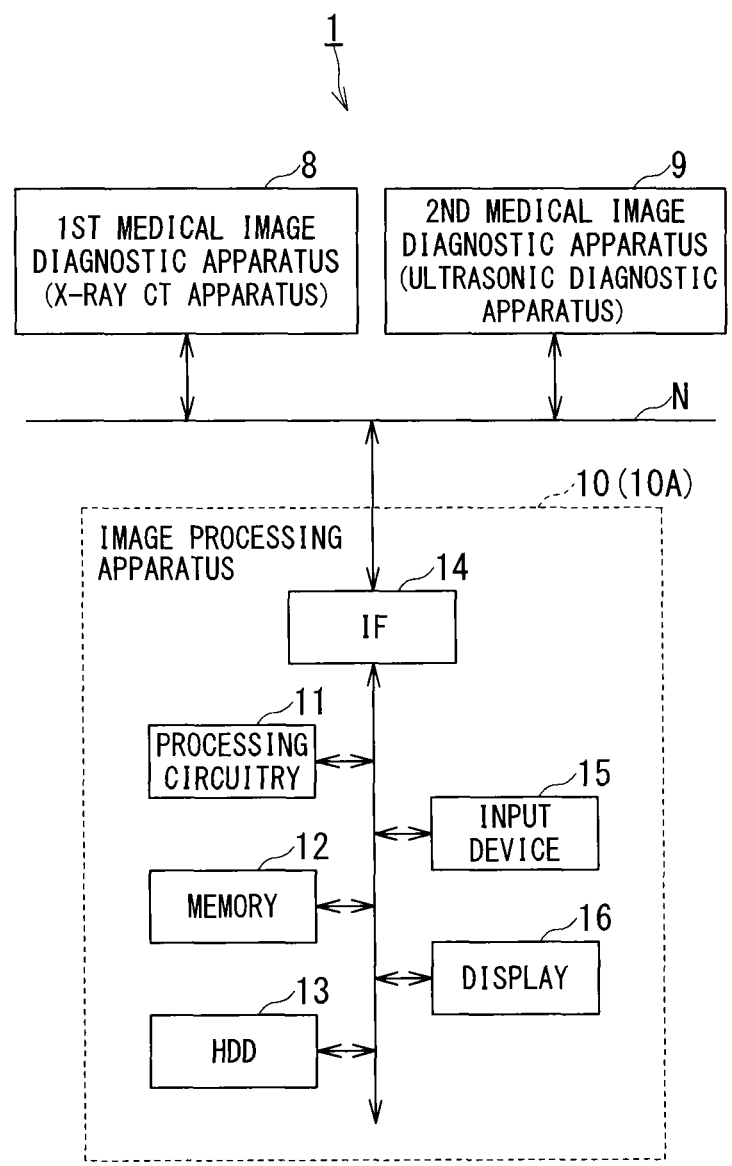
FIG. 1 is a diagram showing a configuration example of an image processing system in which an image processing apparatus according to a first embodiment is installed.

FIG. 1 is a diagram showing a configuration example of an image processing system in which an image processing apparatus according to a first embodiment is installed.

FIG. 1 shows the image processing system 1. The image processing system 1 includes a first medical image diagnostic apparatus 8, a second medical image diagnostic apparatus 9, and the image processing apparatus 10 according to the first embodiment. The case is hereinafter described where the image processing apparatus 10 obtains different types of volume data from the two medical image diagnostic apparatuses 8 and 9. Alternatively, the case may be adopted where the image processing apparatus 10 obtains different types of volume data from the single first medical image diagnostic apparatus 8 (or second medical image diagnostic apparatus 9).

The first medical image diagnostic apparatus 8 may be an X-ray CT apparatus, a magnetic resonance imaging (MRI) apparatus or the like that can generate first volume data showing the morphological shape of an object. The first volume data is, for example, a 3D data (heart volume data) including at least the morphological information on a coronary artery that supplies nutrition to a heart in the cardiovascular system. The case of adopting an X-ray CT apparatus as the first medical image diagnostic apparatus 8 is hereinafter described.

The second medical image diagnostic apparatus 9 may be any of an ultrasonic diagnostic apparatus, an MRI apparatus, a nuclear medicine diagnostic apparatus or the like that can generate second volume data showing information corresponding to a position spatially different from the position of the object. The second volume data is, for example, multi-frame 3D data (cardiac wall volume data) including at least pieces of information on endocardial and epicardial morphological shapes among pieces of information on the cardiac walls. The case of adopting an ultrasonic diagnostic apparatus as the second medical image diagnostic apparatus 9 is hereinafter described.

The X-ray CT apparatus 8, the ultrasonic diagnostic apparatus 9, and the image processing apparatus 10 in the image processing system 1 can communicate with each other via a network N, such as a local area network (LAN). The X-ray CT apparatus 8, the ultrasonic diagnostic apparatus 9, and the image processing apparatus 10 may be connected with each other via a picture archiving and communication system (PACS).

X-ray CT apparatus 8 has a computer-based configuration. The X-ray CT apparatus 8 controls a scanner (not shown) to generate heart volume data. The X-ray CT apparatus 8 transfers the heart volume data to the image processing apparatus 10 via the network N. The X-ray CT apparatus 8 can transfer heart volume data via the PACS or via a portable medium, such as a universal serial bus (USB) memory or a DVD. In some cases, the heart volume data is generated by an imaging method. Alternatively, in other cases, the data is generated by a non-imaging method.

The ultrasonic diagnostic apparatus 9 has a computer-based configuration. The ultrasonic diagnostic apparatus 9 controls an ultrasonic probe (not shown) to generate multi-frame cardiac wall volume data. In the case of adopting an ultrasonic probe that includes a 1- or 1.5-row transducer, a 3D region is scanned by the transducer of the ultrasonic probe mechanically vibrating in the row direction. In the case of adopting an ultrasonic probe that includes a multi-row transducer, a 3D region is scanned by electric control. The ultrasonic diagnostic apparatus 9 transmits the multi-frame cardiac wall volume data to the image processing apparatus 10 via the network N. Alternatively, the ultrasonic diagnostic apparatus 9 can transfer the multi-frame cardiac wall volume data via the PACS or a portable medium, such as a USB memory or a DVD.

The image processing apparatus 10 has a computer-based configuration. The image processing apparatus 10 is roughly made of basic hardware that includes a processing circuitry 11 serving as a control device, a memory 12, a hard disk drive (HDD) 13, an interface (IF) 14, an input device (input circuitry) 15, and a display 16. The processing circuitry 11 is mutually connected to each of the hardware configuration elements that configure the image processing apparatus 10 via a bus that serves as a common signal transfer path.

The processing circuitry 11 means any of dedicated and general-purpose CPUs (central processing units), an application specific integrated circuit (ASIC), and a programmable logic device. The programmable logic device may be, for example, any of a simple programmable logic device (SPLD), a complex programmable logic device (CPLD), and a field programmable gate array (FPGA). The processing circuitry 11 achieves the functions shown in FIG. 2 by reading and executing programs stored in the memory 12 (or the HDD 13) or directly implemented in the processing circuitry 11.

Furthermore, the processing circuitry 11 may be configured by a single-piece processing circuitry, or an integrated processor circuitry including multiple independent processing circuitries. In the latter situation, memories 12 for recording programs may be separately provided for the respective processing circuitries. Alternatively, one memory 12 may store programs corresponding to the respective functions of circuitries.

The memory 12 is a storing device that includes a read only memory (ROM) and random access memory (RAM). The memory 12 has functions of storing initial program loading (IPL), a basic input/output system (BIOS), and data, and of being used as a working memory for the processing circuitry 11 and being used for temporary storing of data.

The HDD 13 is a storing device having a configuration where metal disks onto which a magnetic substance has been applied or evaporated are stored in a reading device (not shown) in an undetachable manner. The HDD 13 has a function of storing programs (including not only application programs but also an operating system (OS), and the like) and various data items that are installed in the image processing apparatus 10.

The IF 14 includes a connector in conformity with parallel connection standards or serial connection standards. The IF 14 performs communication control in conformity with corresponding standards, and has a function that can be connected to the network N via telephone lines, thereby allowing the image processing apparatus 10 to be connected to the network N.

The input device 15 includes a keyboard, a mouse and the like that allow a reader (operator), such as a doctor, to operate. An input signal according to an operation through the input device 15 is transmitted to the processing circuitry 11 via a bus.

The display 16 may be a typical display and output device, such as a liquid crystal display or an organic light emitting diode (OLED), and displays generated image data according to the control by the processing circuitry 11.

Figure 2:
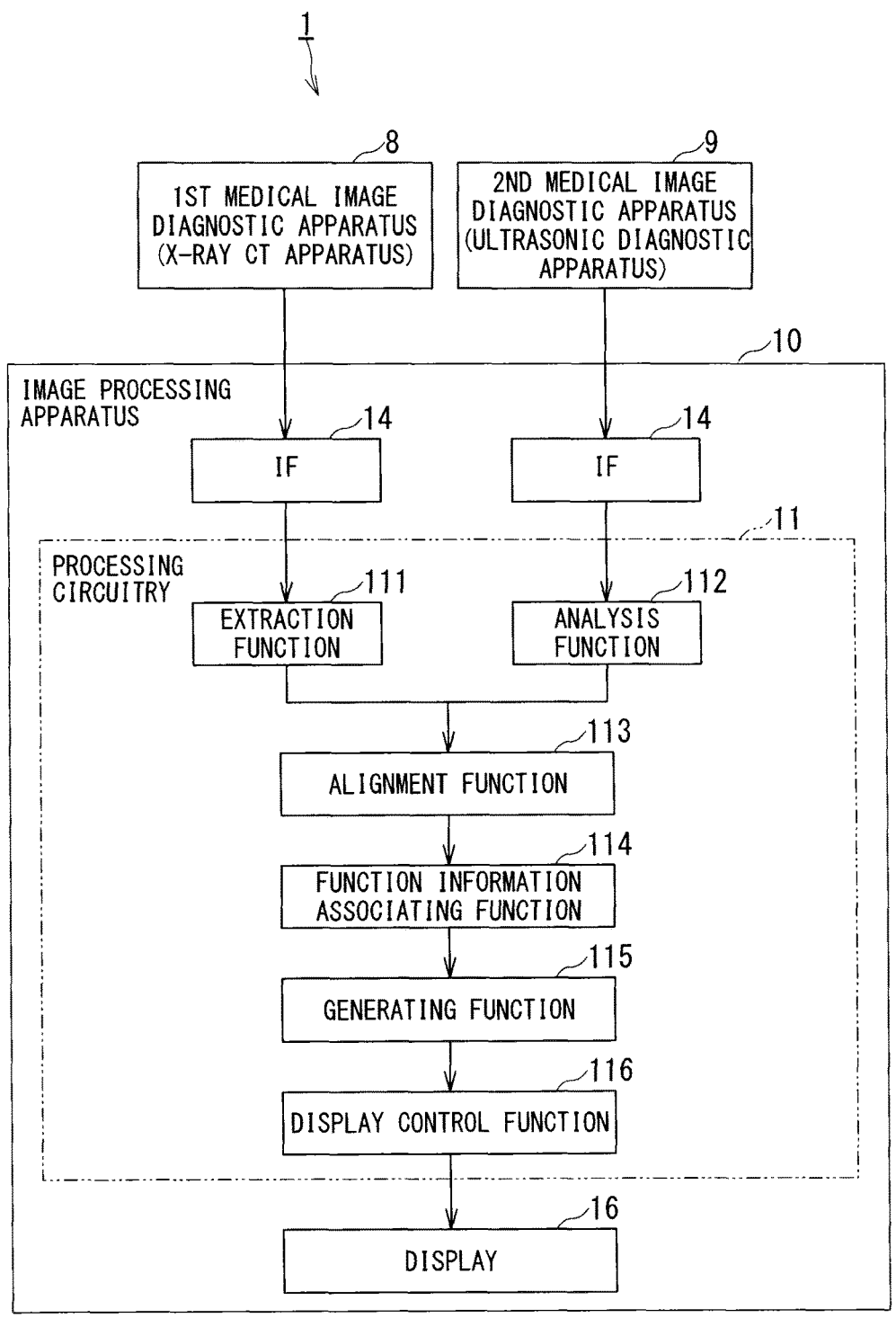
FIG. 2 is a block diagram showing functions of the image processing apparatus according to the first embodiment.

FIG. 2 is a block diagram showing functions of the image processing apparatus 10 according to the first embodiment.

Execution of the programs by the processing circuitry 11 allows the image processing apparatus 10 to function as an extraction function 111, an analysis function 112, an alignment function 113, a function information associating function 114, a generating function 115, and a display control function 116. The functions 111 to 116 are described exemplifying the case of functioning as software. Alternatively, some of or all the functions 111 to 116 may be included in the image processing apparatus 10 in a form of hardware. In some cases, the image processing apparatus 10 includes a drive (not shown) where a portable medium can be mounted.

The processing circuitry 11 can obtain the first volume data showing the morphological shape of the object from the first medical image diagnostic apparatus 8, and the second volume data showing a position spatially different from the position of the object from the second medical image diagnostic apparatus 9, and provide information on the second volume data to the position of the object in the first volume data. Referring to FIG. 2, the case is described where the heart volume data as the first volume data is obtained from the X-ray CT apparatus 8, which is the first medical image diagnostic apparatus 8, and the cardiac wall volume data (or the cardiac function volume data including the cardiac wall volume data to which the cardiac function information is provided) is obtained from the ultrasonic diagnostic apparatus 9, which is the second medical image diagnostic apparatus 9.

Furthermore, in some cases, the processing circuitry 11 provides luminance information (luminance information on a tumor region and the like) in the second volume data to the position of a blood vessel in the heart volume data (or coronary artery volume data where the coronary artery is extracted) as the first volume data.

The extraction function 111 acquires, via the IF 14, the heart volume data obtained by the X-ray CT apparatus 8. The extraction function 111 then applies a segmentation process to the heart volume data, thereby extracting the coronary artery volume data (first volume data) that encompasses at least the coronary artery, from the heart volume data. The extraction function 111 uses a conventional, typical method as the segmentation process.

Figure 3:
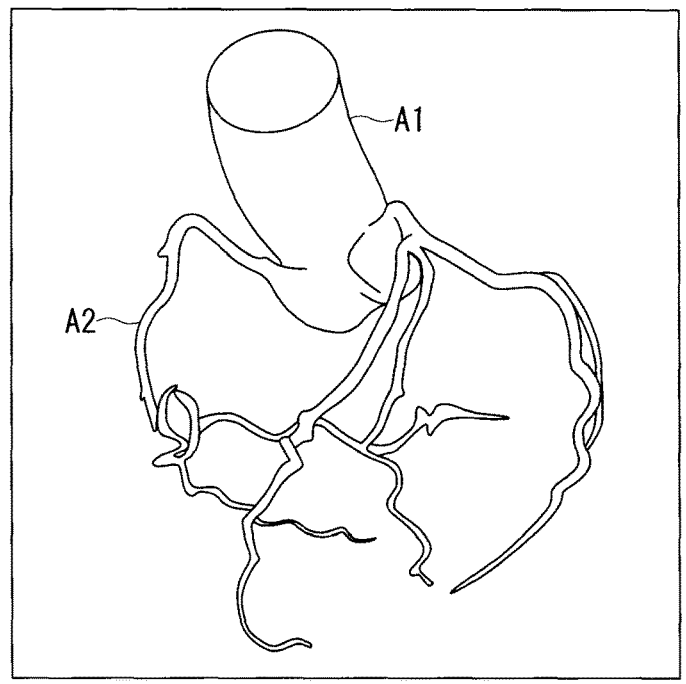
FIG. 3 is a diagram showing an example of a 3D image based on coronary artery volume data.

FIG. 3 is a diagram showing an example of a 3D image based on the coronary artery volume data.

FIG. 3 shows the 3D image obtained by applying a rendering process to the coronary artery volume data encompassing an aorta and a coronary artery. The 3D image encompasses the aorta A1 and the coronary artery A2.

Returning to FIG. 2, the analysis function 112 obtains, via the IF 14, the multi-frame cardiac wall volume data obtained by the ultrasonic diagnostic apparatus 9. The analysis function 112 then analyzes the multi-frame cardiac wall volume data, and calculates the cardiac function information (wall movement information), thereby obtaining multi-time-phase cardiac function volume data (second volume data).

The analysis function 112 may obtain multi-time-phase cardiac function surface data, which is multi-time-phase cardiac function volume data. The cardiac function information is function information on the cardiac wall (including numeric value information, and attribute information on color assigned based on the numeric value information (at least one piece of hue information, lightness information, and chroma information)) obtained by a tracking process using cardiac wall volume data between two frames. The tracking process uses a conventional method, such as pattern matching. Thus, local cardiac function information on endocardial and epicardial cardiac walls can be obtained. More specifically, the cardiac function information may be on the strain of the cardiac wall. However, this information is not necessarily limited thereto. The cardiac function information may be parameters that can be calculated by a tracking process, for example, the displacement, velocity and the like of the cardiac wall.

The cardiac function volume data is data obtained by providing the cardiac function information to contour information of an endocardia or an epicardia of the cardiac wall volume data. The analysis function 112 may be included in the ultrasonic diagnostic apparatus 9.

Figure 4:
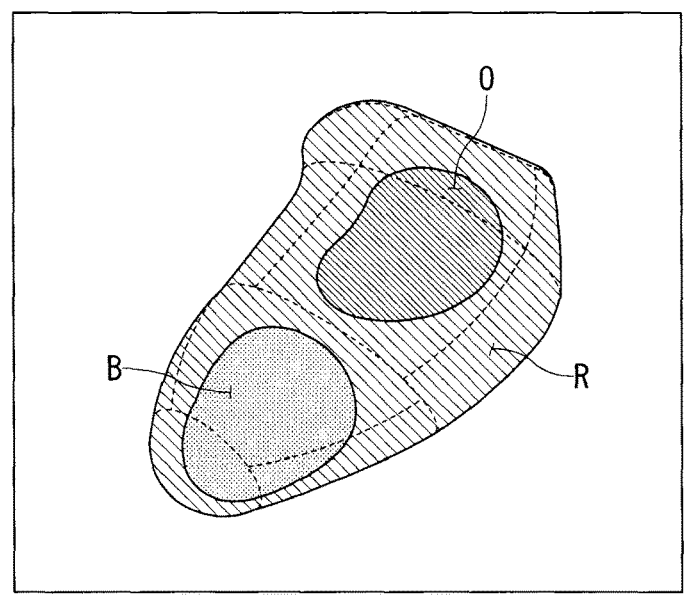
FIG. 4 is a diagram showing an example of the 3D image based on cardiac function volume data.

FIG. 4 is a diagram showing an example of the 3D image based on the cardiac function volume data.

FIG. 4 shows the 3D image obtained by applying a rendering (surface rendering) process to the cardiac function volume data. The 3D image shown in FIG. 4 is based on the cardiac function volume data obtained by applying, to each voxel of the cardiac wall volume data, three hues (blue B, red R and orange O) according to the degree of the numeric value information as the cardiac function information. For the sake of convenience, FIG. 4 shows the case of applying the colors, or three hues, to each voxel of the cardiac wall volume data. However, the technique is not necessarily limited to this case. A color according to one hue, the degree of the numeric value information as the cardiac function information among multiple lightnesses (or chromas), and color attribute information may be applied to each voxel of the cardiac wall volume data. Alternatively, a color according to multiple hues, the degree of the numeric value information as the cardiac function information among multiple lightnesses (or chromas), and color attribute information may be applied to each voxel of the cardiac wall volume data.

Returning to FIG. 2, the alignment function 113 aligns the heart volume data with the cardiac wall volume data, thereby allowing the spatial coordinates to coincide with each other. For example, the alignment function 113 overlays an MPR image based on the heart volume data and an MPR image based on the cardiac wall volume data with each other and displays the overlaid images, and aligns the MPR sectional positions with each other at the same section through manual operations, such as movement and rotation, thereby allowing both the 3D positions to coincide with each other. Alternatively, the alignment function 113 automatically aligns the 3D positions using a conventional technique, such as pattern matching, for example.

When the alignment function 113 aligns the heart volume data with the cardiac wall volume data, this function may, for example, convert the spatial coordinates of the cardiac wall volume data into the spatial coordinates of the heart volume data, convert the spatial coordinates of the heart volume data into the spatial coordinates of the cardiac wall volume data, or convert the spatial coordinates of the heart volume data and the cardiac wall volume data into reference spatial coordinates. In the case where the spatial coordinates of the volume data items have already coincided with each other during image collection of the heart volume data and the cardiac wall volume data, the image processing apparatus 10 does not require the alignment function 113.

The function information associating function 114 receives the heart volume data and the cardiac wall volume data that have spatial coordinates not coinciding with each other, and information showing the relative positional relationship between the spatial coordinates of the volume data items. Alternatively, the function information associating function 114 receives the heart volume data and the cardiac wall volume data which have spatial coordinates coinciding with each other through alignment by the alignment function 113 or which have spatial coordinates having spatial coordinates having already coincided with each other during image collection.

The function information associating function 114 then associates the cardiac function information in the cardiac function volume data, generated by analyzing the cardiac wall volume data, with the coronary artery (front surface) in the coronary artery volume data, extracted from the heart volume data, on the basis of input information into the function information associating function 114. That is, the function information associating function 114 determines regions in the cardiac function volume data for the respective voxels showing the coronary artery in the coronary artery volume data, and associates pieces of the cardiac function information in the region determined for the respective voxels with these voxels. The function information associating function 114 may associate pieces of the cardiac function information in the cardiac function volume data in the substantially same cardiac time phase as the cardiac time phase of the coronary artery volume data with the respective voxels showing the coronary artery of the coronary artery volume data or the cardiac function information in a cardiac time phase including the lowest cardiac function. Furthermore, it is preferred that the function information associating function 114 determine the regions in the cardiac function volume data for the respective voxels showing the coronary artery in the first volume data after alignment, according to the distances from the cardiac function volume data with respect to the voxels showing the coronary artery.

In the case where the coronary artery volume data and the cardiac function volume data that have spatial coordinates coinciding with each other are input into the function information associating function 114, this function information associating function 114 determines voxels that are each closest to a corresponding one of the voxels showing the centerline of the coronary artery in the coronary artery volume data among the multiple voxels in the cardiac function volume data. In this case, the function information associating function 114 associates the pieces of cardiac function information on the determined voxels with the respective voxels showing the coronary artery corresponding to the voxels showing the centerline of the coronary artery. The voxels showing the coronary artery corresponding to the voxels showing the centerline of the coronary artery are, for example, voxels where the sections of the centerline including the voxels indicating the centerline of the coronary artery coincide with the front surface of the coronary artery.

The coronary artery volume data and the cardiac function volume data that have spatial coordinates coinciding with each other have 3D coordinate values in the same coordinate space. Accordingly, the function information associating function 114 calculates the 3D distances between a prescribed voxel showing the centerline of the coronary artery included in the coronary artery volume data and the multiple voxels in the cardiac function volume data. This calculation can determine the voxel that is in the cardiac function volume data and closest to the prescribed voxel. The function information associating function 114 can then associate the piece of cardiac function information on the voxel in the cardiac function volume data closest to the prescribed voxel with the voxel showing the coronary artery corresponding to the prescribed voxel.

Here, the centerline of the coronary artery encompassed by the coronary artery volume data is a curve (center line) that passes through the center of the coronary artery and is extracted on the basis of the coordinate information on the coronary artery. Any conventional method may be applied to implement the method of extracting the center line of the coronary artery from the coordinate information on the coronary artery. For instance, one example of the method of extracting the center line uses a method that calculates the barycenters of the inner wall on sections obtained by sectioning the coronary artery at regular intervals, and connects these barycenters with a curve using spline interpolation.

The multiple voxels, included in the coronary artery volume data, showing the centerline of the coronary artery may be at regular intervals or irregular intervals. The multiple voxels, included in the coronary artery volume data, showing the centerline of the coronary artery may be arbitrarily changed.

Figure 5:
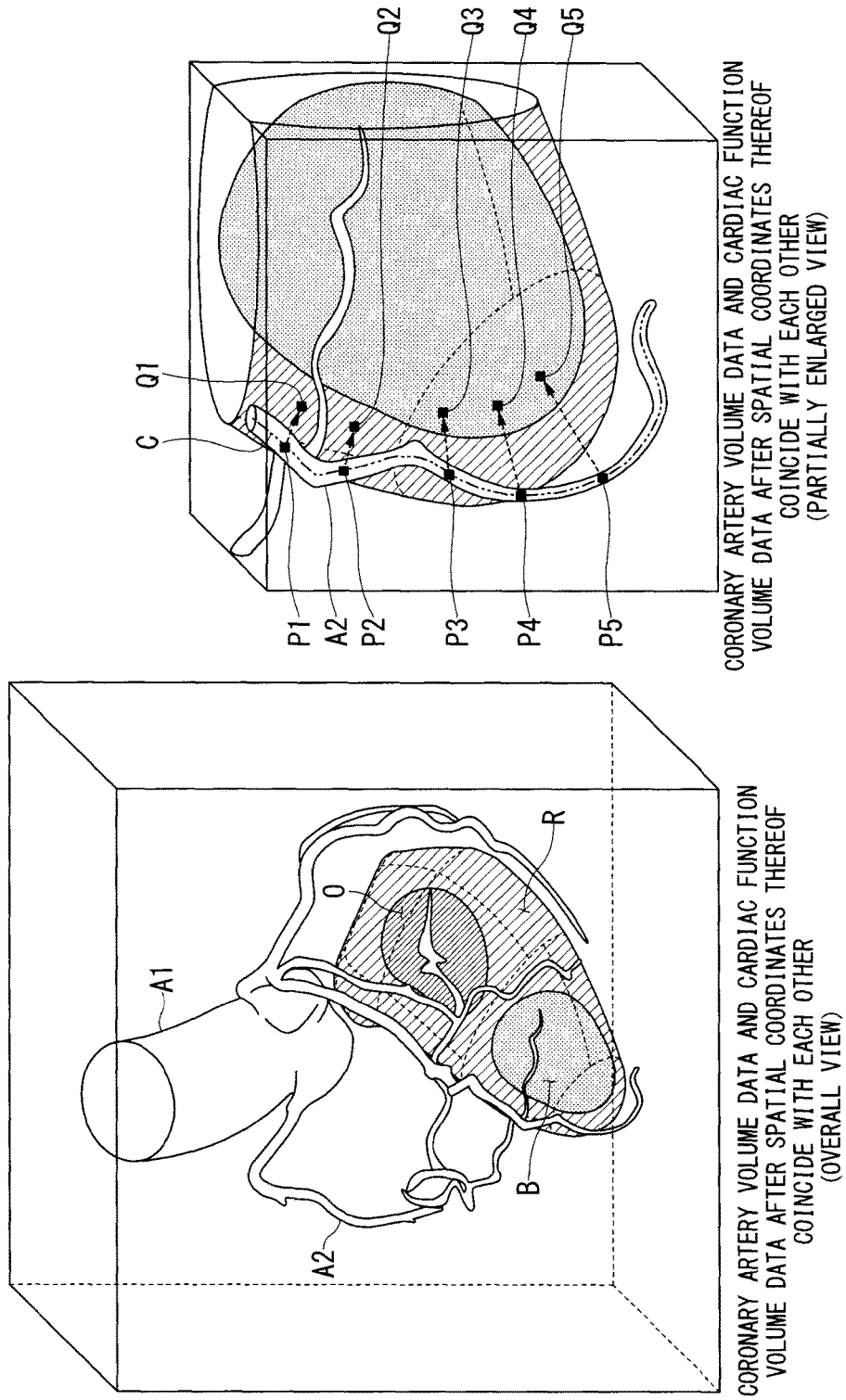
FIGS. 5A and 5B are diagrams showing an example of the coronary artery volume data and the cardiac function volume data after spatial coordinates thereof coincide with each other.

FIGS. 5A and 5B are diagrams showing an example of the coronary artery volume data and the cardiac function volume data after spatial coordinates thereof coincide with each other.

FIG. 5A shows an overall view of the coronary artery volume data and the cardiac function volume data that have spatial coordinates coinciding with each other. FIG. 5B shows a partially enlarged view of the coronary artery volume data and the cardiac function volume data that have spatial coordinates coinciding with each other. FIG. 5B shows multiple voxels P1 to P5 on the centerline C of the coronary artery A2 included in the coronary artery volume data. Voxels Q1 to Q5 closest to the respective voxels P1 to P5 on the 3D coordinates in the cardiac function volume data are determined.

Here, one voxel closest to each of the multiple voxels, included in the coronary artery volume data, showing the centerline of the coronary artery and voxels surrounding the closest voxel may be determined from among the multiple voxels in the cardiac function volume data. In such a case, the average value of the pieces of cardiac function information on the determined one voxel and the surrounding voxels are associated with each of voxels that indicate the centerline of the coronary artery. In this case, the average value may be a simple addition average value, or a weighted average value according to the distance.

Alternatively, the multiple voxels within a certain distance from each of the multiple voxels, included in the coronary artery volume data, showing the centerline of the coronary artery may be determined from among the multiple voxels of the cardiac function volume data. In such a case, the average value of the pieces of cardiac function information on the determined multiple voxels are associated with each of voxels showing the centerline of the coronary artery. In this case, the average value may be a simple addition average value, or a weighted average value according to the distance.

Returning to FIG. 2, the generating function 115 provides the cardiac function information associated with the coronary artery by the function information associating function 114 at the position of the coronary artery of the coronary artery volume data, thereby generating third volume data. The voxel showing the coronary artery in the coronary artery volume data holds the voxel values (CT values). Accordingly, the generating function 115 converts the voxel values showing the coronary artery into the voxel values according to the degree of the numeric value information, which is the cardiac function information, and to the color attribute information.

The display control function 116 applies the rendering process to the third volume data generated by the generating function 115, and causes the display 16 to display the data as a 3D image.

Figure 6:
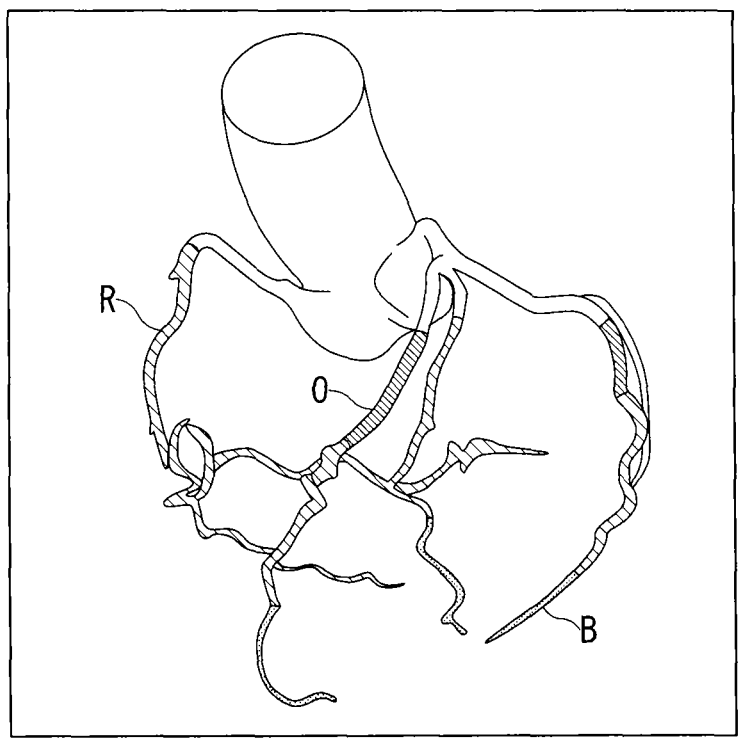
FIG. 6 is a diagram showing an example of the 3D image based on third volume data.

FIG. 6 is a diagram showing an example of the 3D image based on the third volume data.

FIG. 6 shows the 3D image based on the third volume data generated by converting the voxel values showing the coronary artery shown in FIG. 3 into the voxel values for representing the colors, or three hues (blue B, red R, orange O), corresponding to FIG. 4. The 3D image shown in FIG. 6 allows the operator to visually identify the entire morphological information on the three-dimensionally distributed coronary artery and the cardiac function information at the same time with no 3D image turning operation.

The displayed 3D image shown in FIG. 6 allows both the morphological information on the coronary artery and the cardiac function information to be represented using the morphological shape of the coronary artery. If there is a place where a Strain level suddenly falls down, there becomes constricted or occludes and bloodstream is likely to penetrate to myocardium caused by there. The place can be judged to be a blood vessel where a diagnosis or a treatment in detail is necessary. Unlike the conventional case, the operator is not required to perform the turning operation for the 3D image for viewing the rear side of the 3D image. The operator can easily grasp the morphological information on the coronary artery and the cardiac function information.

The image processing apparatus 10 and the image processing method according to the first embodiment can present the operator with the cardiac function information itself, such as the strain value. Furthermore, the image processing apparatus 10 and the image processing method according to the first embodiment can omit the turning operation (turning operation for the direction of line of sight) for the 3D image by the operator for exhaustively identifying the vascular narrowing portion and the cardiac malfunctioning portion. Consequently, the operational load on the operator can be reduced.

Second Embodiment

An image processing apparatus (image processing apparatus 10A shown in FIG. 7) according to a second embodiment has a configuration equivalent to that of the image processing apparatus 10 shown in FIG. 1. Accordingly, the description is omitted.

Figure 7:
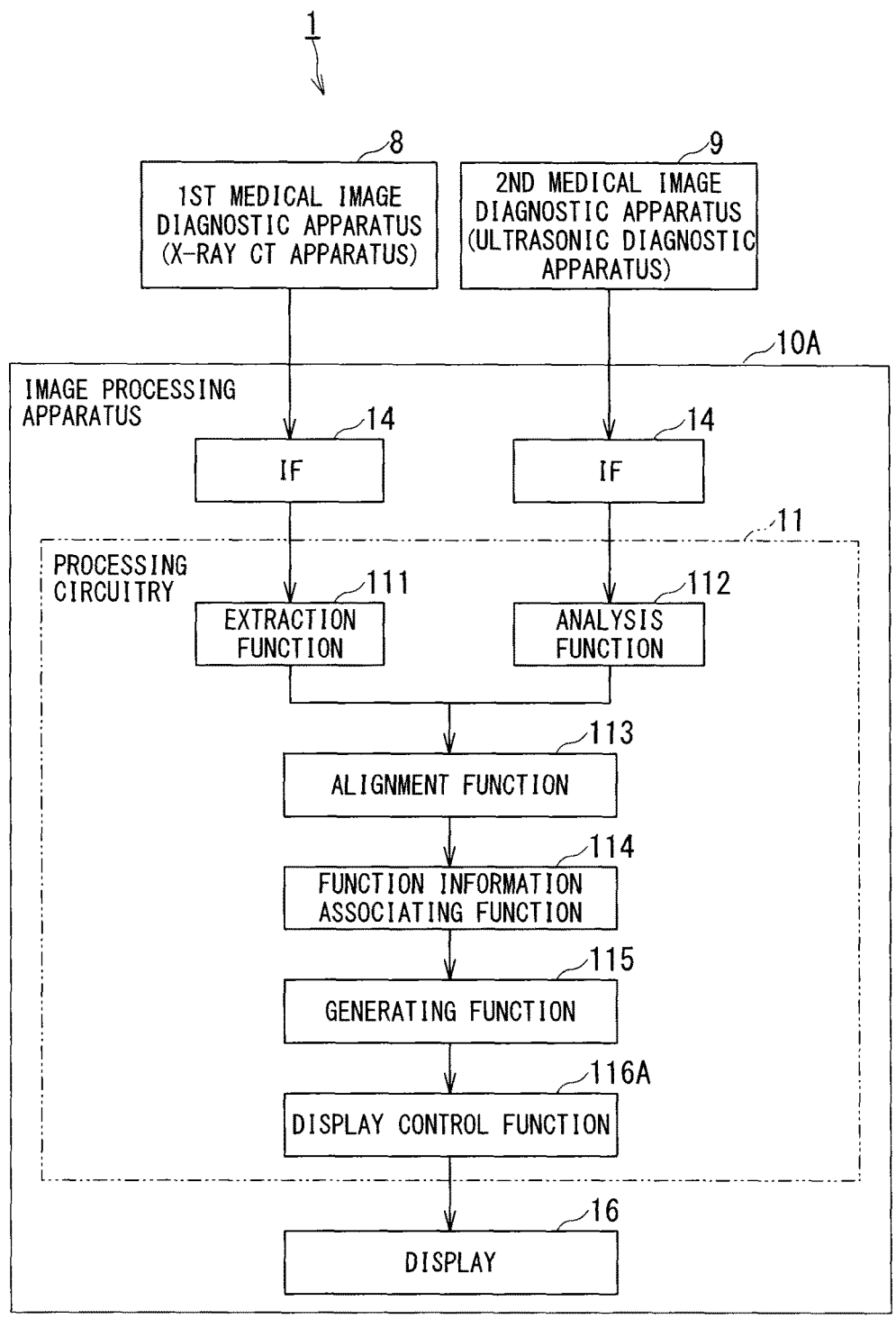
FIG. 7 is a block diagram showing functions of the image processing apparatus according to a second embodiment.

FIG. 7 is a block diagram showing functions of the image processing apparatus 10A according to the second embodiment.

Execution of the programs by the processing circuitry 11 allows the image processing apparatus 10A to function as an extraction function 111, an analysis function 112, an alignment function 113, a function information associating function 114, a generating function 115, and a display control function 116A. The functions 111 to 116A are described exemplifying the case of functioning as software. Alternatively, some of or all the functions 111 to 116A may be included in the image processing apparatus 10A in a form of hardware. In some cases, the image processing apparatus 10A includes a drive where a portable medium can be mounted (not shown).

Referring to FIG. 7, as with FIG. 2, the case is described that obtains the heart volume data (or coronary artery volume data where the coronary artery is extracted), which is the first volume data, from the X-ray CT apparatus 8, which is the first medical image diagnostic apparatus B, and obtains the cardiac wall volume data (or the cardiac function volume data including the cardiac wall volume data to which the cardiac function information is provided) from the ultrasonic diagnostic apparatus 9, which is the second medical image diagnostic apparatus 9.

In the image processing apparatus 10A shown in FIG. 7, the same symbols are assigned to the same components as those in the image processing apparatus 10 shown in FIG. 2. The description of these components is omitted.

The display control function 116A causes the display 16 to display the sectional image (MPR image) taken along any section based on the third volume data generated by the generating function 115, and a display image including the sectional image.

Figure 8:
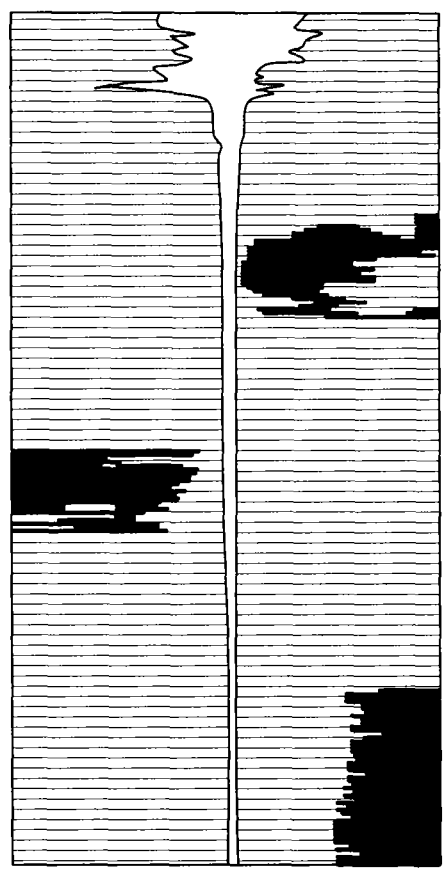
FIG. 8 is a diagram showing a conventional MPR image.

FIG. 8 is a diagram showing a conventional MPR image.

The conventional MPR image shown in FIG. 8 is an MPR image generated along the centerline of the coronary artery, and is generally referred to as "curved MPR". The conventional MPR image shown in FIG. 8 typically holds the CT values.

Figure 9:
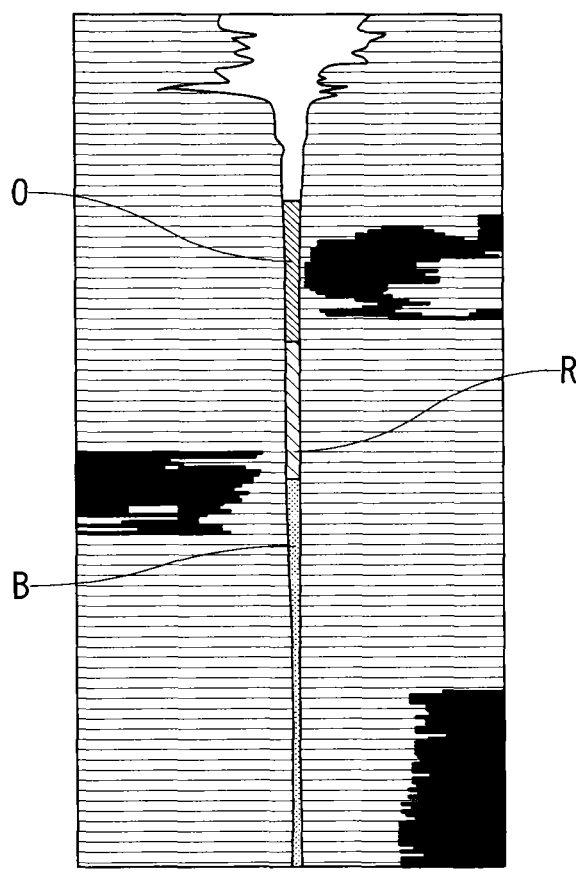
FIG. 9 is a diagram showing an example of an MPR image based on the third volume data.

FIG. 9 is a diagram showing an example of an MPR image based on the third volume data.

FIG. 9 shows the MPR image based on the third volume data generated by converting the voxel data showing the coronary artery into the voxel values for representing the colors, or three hues (blue B, red R, orange O), corresponding to FIG. 4. The MPR image shown in FIG. 9 allows the operator to visually identify the entire morphological information on the three-dimensionally distributed coronary artery and the cardiac function information at the same time.

The displayed MPR image shown in FIG. 9 includes the voxels of the MPR image showing the coronary artery and shows the shape, specifically the thickness, of the coronary artery, to which the voxel values that are according to the degree of the cardiac function information, for example, the strain values and are of the voxels are provided. Consequently, the operator can identify presence or absence of narrowing and presence or absence of malfunctioning at a glance.

Figure 10:
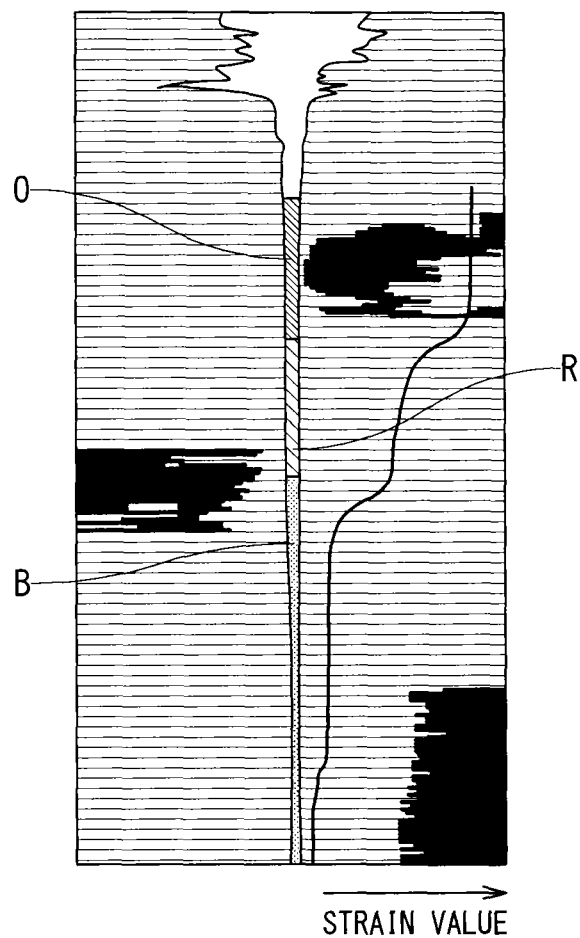
FIG. 10 is a diagram showing an example of a display image based on the third volume data.

FIG. 10 is a diagram showing an example of a display image based on the third volume data.

FIG. 10 shows the display image including the MPR image (image shown in FIG. 9) based on the third volume data generated by converting the voxel values showing the coronary artery into the voxel values for representing the colors, or three hues (blue B, red R and orange O) corresponding to FIG. 4, on which the a graph of the cardiac function information, e.g., the strain values, corresponding to the voxel values showing the coronary artery is overlaid. The displayed display image shown in FIG. 10 can allow the operator to enjoy the advantageous effects of the displayed MPR image shown in FIG. 9 and visually identify the distribution of strain values. The operator can thus grasp the degree of malfunctioning in further detail.

The image processing apparatus 10A and the image processing method according to the second embodiment can present the operator with the cardiac function information itself, such as the strain value. Furthermore, the image processing apparatus 10A and the image processing method according to the second embodiment can omit the turning operation (turning operation for the direction of line of sight) for the 3D image by the operator for exhaustively identifying the vascular narrowing portion and the cardiac malfunctioning portion. Consequently, the operational load on the operator can be reduced.

Third Embodiment

A medical image diagnostic apparatus according to a third embodiment includes the configuration elements 111 to 116 of the image processing apparatus 10 shown in FIG. 2. The case is hereinafter described where the configuration elements 111 to 116 of the image processing apparatus 10 shown in FIG. 2 are included in an X-ray CT apparatus 58 (shown in FIG. 11), which is a medical image diagnostic apparatus capable of generating the heart volume data. Alternatively, the elements may be included in an ultrasonic diagnostic apparatus 59 (shown in FIG. 11), which is a medical image diagnostic apparatus capable of generating the multi-frame cardiac wall volume data.

Figure 11:
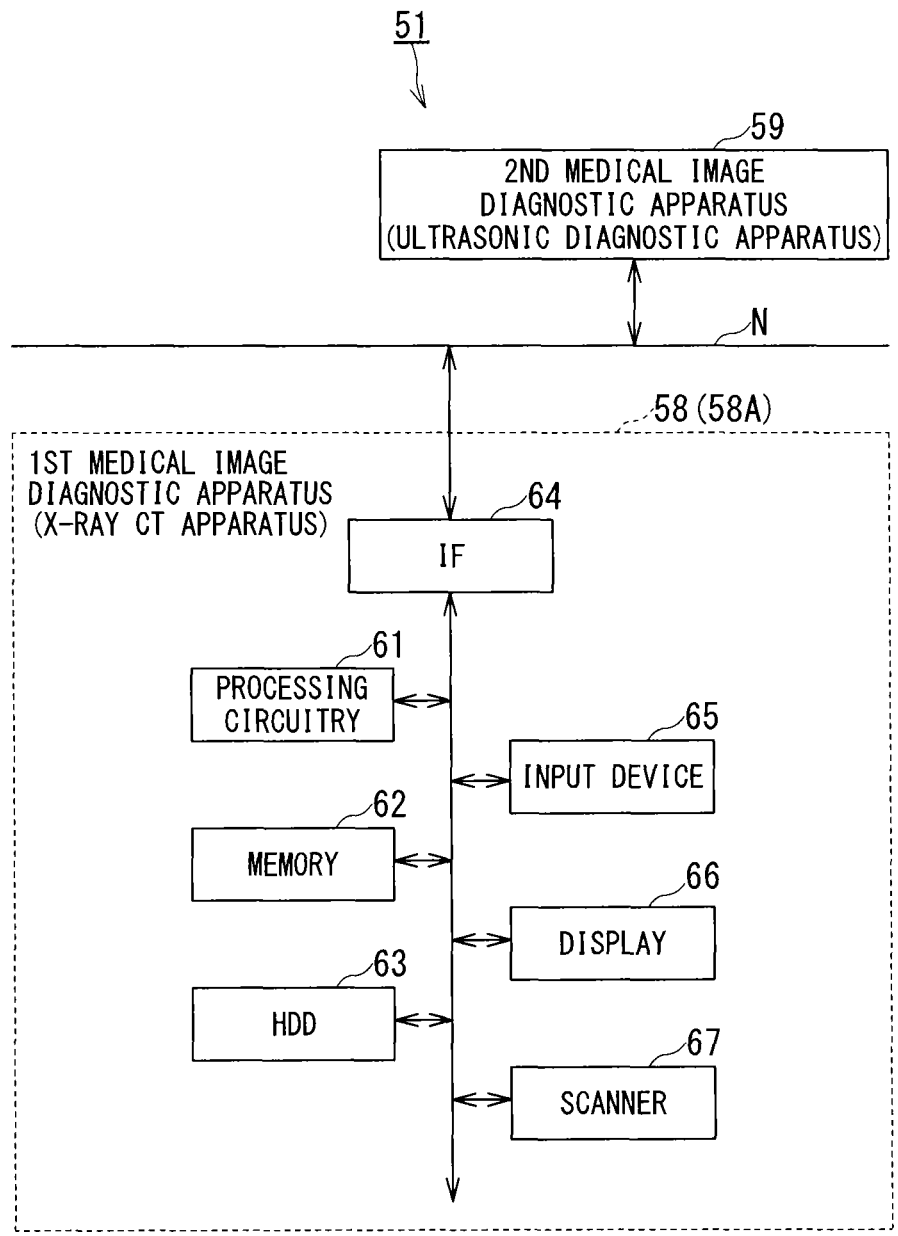
FIG. 11 is a diagram showing a configuration example of an image processing system in which a medical image diagnostic apparatus according to a third embodiment is installed.

FIG. 11 is a diagram showing a configuration example of an image processing system in which a medical image diagnostic apparatus according to a third embodiment is installed.

FIG. 11 shows the image processing system 51. The image processing system 51 includes: the first medical image diagnostic apparatus 58, which is the medical image diagnostic apparatus according to the third embodiment; and the second medical image diagnostic apparatus 59. The case is hereinafter described where the first medical image diagnostic apparatus 58 obtains volume data of a type different than that of the volume data generated by the first medical image diagnostic apparatus 58 from the other second medical image diagnostic apparatus 59. Alternatively, a configuration may be adopted where the single first medical image diagnostic apparatus 58 generates different types of volume data.

The first medical image diagnostic apparatus 58 may be any of an X-ray CT apparatus and an MRI apparatus that can generate first volume data showing the morphological shape of the object. The first volume data is, for example, heart volume data. The case of adopting an X-ray CT apparatus as the first medical image diagnostic apparatus 58 is hereinafter described.

The second medical image diagnostic apparatus 59 may be any of an X-ray CT apparatus, an ultrasonic diagnostic apparatus, an MRI apparatus, and a nuclear medicine diagnostic apparatus that can generate second volume data showing information corresponding to a position spatially different from the position of the object. The second volume data is, for example, multi-frame cardiac wall volume data. The case of adopting an ultrasonic diagnostic apparatus as the second medical image diagnostic apparatus 59 is hereinafter described.

The X-ray CT apparatus 58 and the ultrasonic diagnostic apparatus 59 in the image processing system 51 can communicate with each other via the network N, such as an LAN. The X-ray CT apparatus 58 and the ultrasonic diagnostic apparatus 59 can communicate with each other via the PACS.

The X-ray CT apparatus 58 is roughly made of basic hardware that includes processing circuitry 61 serving as a control device, a memory 62, an HDD 63, an IF 64, an input device 65, a display 66, a scanner 67. The processing circuitry 61 is mutually connected to each of the hardware configuration elements that configure the X-ray CT apparatus 58 via a bus, which serves as a common signal transfer path.

The ultrasonic diagnostic apparatus 59 has a computer-based configuration. The ultrasonic diagnostic apparatus 59 controls an ultrasonic probe (not shown) to generate multi-frame cardiac wall volume data. In the case of adopting an ultrasonic probe that includes a 1- or 1.5-row transducer, a 3D region is scanned by the transducer of the ultrasonic probe mechanically vibrating in the row direction. In the case of adopting an ultrasonic probe that includes a multi-row transducer, a 3D region is scanned by electric control. The ultrasonic diagnostic apparatus 59 transmits the multi-frame cardiac wall volume data to the X-ray CT apparatus 58 via the network N. Alternatively, the ultrasonic diagnostic apparatus 59 can transfer the multi-frame cardiac wall volume data via the PACS or a portable medium, such as a USB memory or a DVD.

The processing circuitry 61 of the X-ray CT apparatus 58 is a control device having a configuration analogous to that of the processing circuitry 11 shown in FIG. 1. The processing circuitry 61 executes programs stored in the memory 62. Alternatively, the processing circuitry 61 has a function of loading, in the memory 62, programs stored in the HDD 63, and programs transferred via the network N, received by the IF 64 and installed in the HDD 63, and then executing the programs.

The memory 62 is a storing device analogous to the memory 12 shown in FIG. 1. The memory 62 has a function of storing IPL, BIOS and data, and of being used as a working memory for the processing circuitry 61 and being used for temporary storing of data.

The HDD 63 is a storing device having a configuration analogous to that of the HDD 13 shown in FIG. 1. The HDD 63 has a function of storing programs (including not only application programs but also OS, and the like) and various data items that are installed in the X-ray CT apparatus 58.

The IF 64 has a configuration analogous to that of the IF 14 shown in FIG. 1. The IF 64 performs communication control in conformity with corresponding standards, and can be connected to the network N via telephone lines, thereby allowing the X-ray CT apparatus 58 to be connected to the network N.

The input device 65 has a configuration analogous to that of the input device 15 shown in FIG. 1. An input signal according to the operation through the input device 65 is transmitted to the processing circuitry 61 via a bus.

The display 66 has a configuration analogous to that of the display 16 shown in FIG. 1.

The scanner 67 is controlled by the processing circuitry 61 to generate the heart volume data. In some cases, the heart volume data is generated by an imaging method. Alternatively, in other cases, the data is generated by a non-imaging method.

Figure 12:
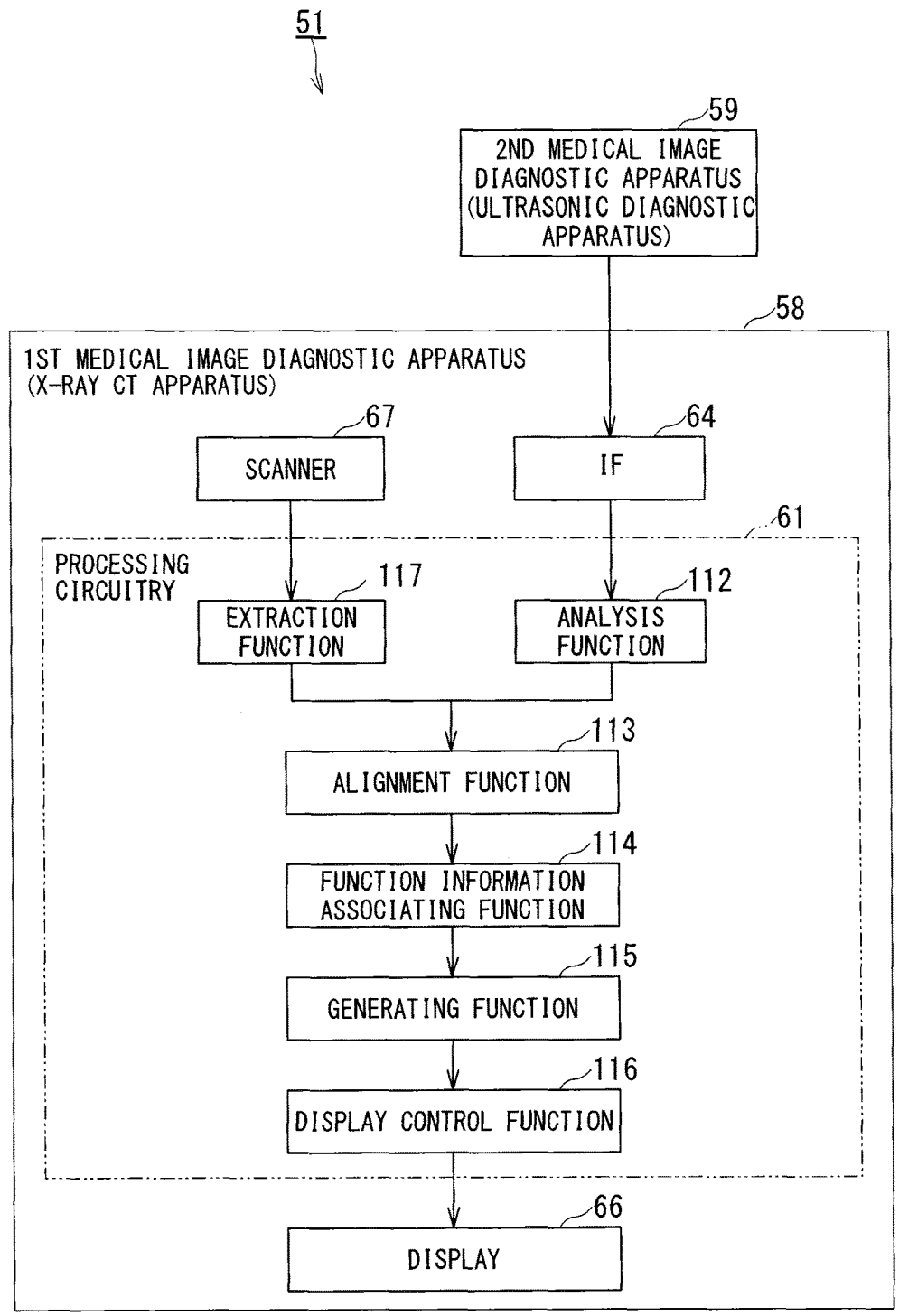
FIG. 12 is a block diagram showing functions of the medical image diagnostic apparatus according to the third embodiment.

FIG. 12 is a block diagram showing functions of the medical image diagnostic apparatus according to the third embodiment.

Execution of the programs by the processing circuitry 61 allows the X-ray CT apparatus 58, which is the medical image diagnostic apparatus, to function as an analysis function 112, an alignment function 113, a function information associating function 114, a generating function 115, a display control function 116, and an extraction function 117. The functions 112 to 117 are described exemplifying the case of functioning as software. Alternatively, some of or all the functions 112 to 117 may be included in the X-ray CT apparatus 58 in a form of hardware. In some cases, the X-ray CT apparatus 58 includes a drive where a portable medium can be mounted (not shown).

The processing circuitry 61 can generate one of the first volume data showing the morphological shape of the object and the second volume data showing information corresponding to a position spatially different from the position of the object, obtain the other one of the first volume data and the second volume data from the medical image diagnostic apparatus, and provide information in the second volume data to the position of the object in the first volume data. Referring to FIG. 12, the case is described where the heart volume data which is the first volume data is generated by the scanner 67, and the cardiac wall volume data (or the cardiac function volume data including the cardiac wall volume data to which the cardiac function information is provided) is obtained from the ultrasonic diagnostic apparatus 59, which is the second medical image diagnostic apparatus 59.

Furthermore, in some cases, the processing circuitry 61 provides luminance information (luminance information on a tumor region and the like) in the second volume data to the position of a blood vessel in the heart volume data (or coronary artery volume data where the coronary artery is extracted) as the first volume data.

In FIG. 12, the same symbols are assigned to the same components as those shown in FIG. 2. The description of these components is omitted.

The extraction function 117 obtains the heart volume data generated by the scanner 67. As with the extraction function 111 (shown in FIG. 2), the extraction function 117 then applies the segmentation process to the heart volume data, thereby extracting the coronary artery volume data (first volume data) that encompasses at least the coronary artery, from the heart volume data.

The display control function 116 causes the display 66 to display the 3D image (shown in FIG. 6).

The medical image diagnostic apparatus (X-ray CT apparatus 58) according to the third embodiment can present the operator with the cardiac function information itself, such as the strain value. Furthermore, the medical image diagnostic apparatus according to the third embodiment can omit the turning operation (turning operation for the direction of line of sight) for the 3D image by the operator for exhaustively visually identifying the vascular narrowing portion and the cardiac malfunctioning portion. Consequently, the operational load on the operator can be reduced.

Fourth Embodiment

A medical image diagnostic apparatus according to a fourth embodiment includes the configuration elements 111 to 116A of the image processing apparatus 10A shown in FIG. 7. The case is hereinafter described where the configuration elements 111 to 116A of the image processing apparatus 10A shown in FIG. 7 are included in an X-ray CT apparatus 58A (shown in FIG. 13), which is a medical image diagnostic apparatus capable of generating the heart volume data. Alternatively, these elements may be included in the ultrasonic diagnostic apparatus 59 (shown in FIG. 13), which is the medical image diagnostic apparatus capable of generating the multi-frame cardiac wall volume data. The X-ray CT apparatus 58A (shown in FIG. 13), which is the medical image diagnostic apparatus according to fourth embodiment, has a configuration equivalent to those of the X-ray CT apparatus 58 shown in FIG. 11. Accordingly, the description is omitted.

Figure 13:
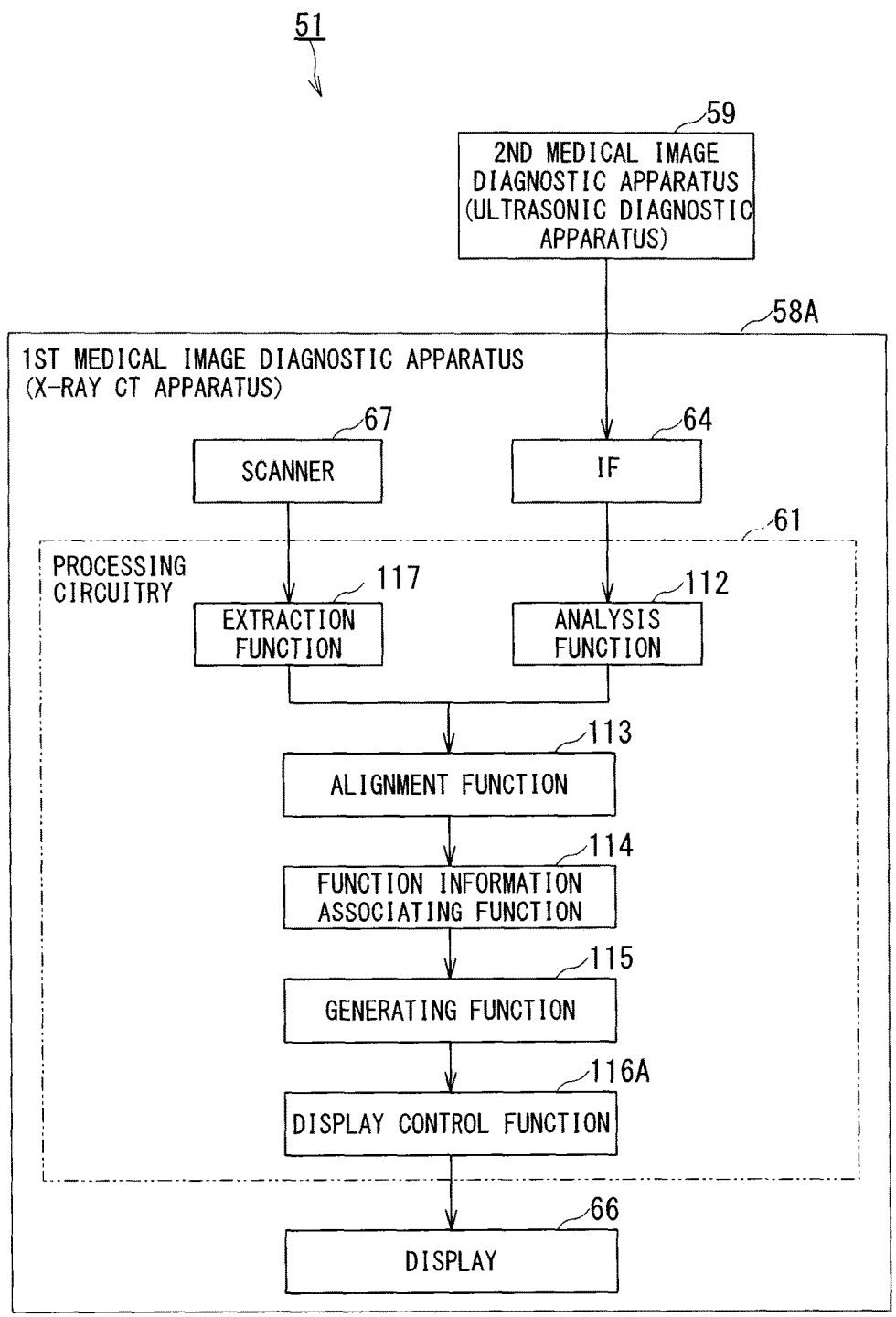
FIG. 13 is a block diagram showing functions of the medical image diagnostic apparatus according to a fourth embodiment.

FIG. 13 is a block diagram showing functions of the medical image diagnostic apparatus according to the fourth embodiment.

Execution of the programs by the processing circuitry 61 allows the X-ray CT apparatus 58A, which is the medical image diagnostic apparatus, to function as an analysis function 112, an alignment function 113, a function information associating function 114, a generating function 115, a display control function 116A, and an extraction function 117. The functions 112 to 117 are described exemplifying the case of functioning as software. Alternatively, some of or all the functions 112 to 117 may be included in the X-ray CT apparatus 58A in a form of hardware. In some cases, the X-ray CT apparatus 58A includes a drive where a portable medium can be mounted (not shown).

Referring to FIG. 13, as with FIG. 12, the case is described where the heart volume data (or coronary artery volume data where the coronary artery is extracted), which is the first volume data, is generated by the scanner 67, and the cardiac wall volume data (or the cardiac function volume data including the cardiac wall volume data to which cardiac function information is provided) is obtained from the ultrasonic diagnostic apparatus 59, which is the second medical image diagnostic apparatus 59.

In the X-ray CT apparatus 58A shown in FIG. 13, the same symbols are assigned to the same components as those of the X-ray CT apparatus 58 shown in FIG. 12. The description of these components is omitted.

The display control function 116A causes the display 66 to display the sectional image (shown in FIG. 9) taken at any section based on the third volume data generated by the generating function 115, and the display image (shown in FIG. 10) including sectional image.

The medical image diagnostic apparatus (X-ray CT apparatus 58A) according to the fourth embodiment can present the operator with the cardiac function information itself, such as the strain value. The medical image diagnostic apparatus 58A according to the fourth embodiment can omit the turning operation (turning operation for the direction of line of sight) for the 3D image by the operator for exhaustively visually identifying the vascular narrowing portion and the cardiac malfunctioning portion. Consequently, the operational load on the operator can be reduced.

Variation Example

With reference to the first to fourth embodiments, the cases have been described where the first volume data is the coronary artery volume data, and the second volume data is the cardiac function volume data, and the cardiac function information in the cardiac function volume data is provided to the position of the blood vessel in the coronary artery volume data. That is, in the first to fourth embodiments, the cases have been described where the volume data including cardiac information is used to provide the function information to the position of the object. However, the present invention is not limited to the case. Only with the first volume data showing the morphological shape of the object and the second volume data showing information corresponding to a position spatially different from the position of the object, information can be provided to the position of the object.

For example, the present invention is applicable to the case where the first volume data is head volume data showing a head vascular morphological shape, and the second volume data is brain function volume data showing the functions of a brain, and brain function information in the brain function volume data is provided to the position of the head vascular position in the head volume data. The brain function volume data is obtained, for example, by an MRI apparatus as the second medical image diagnostic apparatus 9 (second medical image diagnostic apparatus 59) using functional-MRI (f-MRI) that is a method of visualizing hemodynamic responses related to the activities of the brain and spinal cord.

Figure 14:
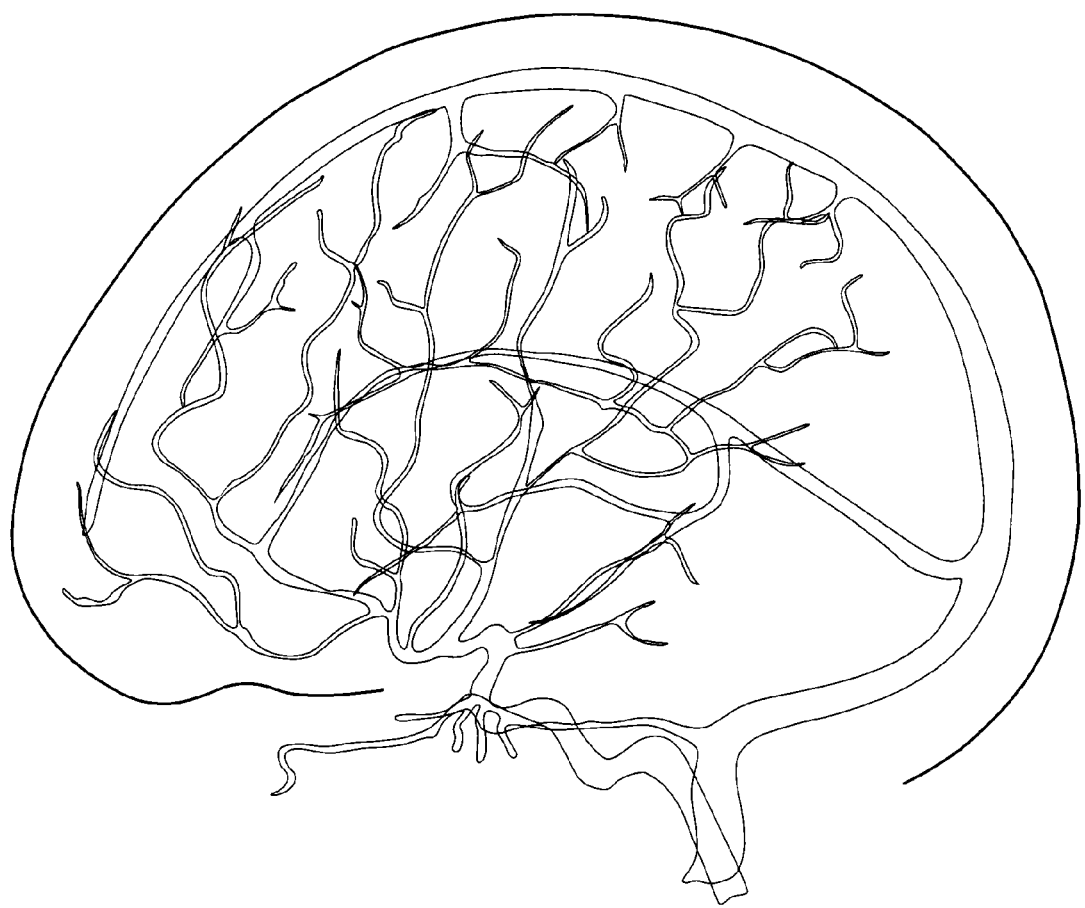
FIG. 14 is a diagram showing an example of a 3D image based on head volume data.

FIG. 14 is a diagram showing an example of the 3D image based on the head volume data. FIG. 14 shows a variation example of FIG. 3.

FIG. 14 shows the 3D image obtained by applying a rendering process to the head volume data including the head blood vessel.

Figure 15:
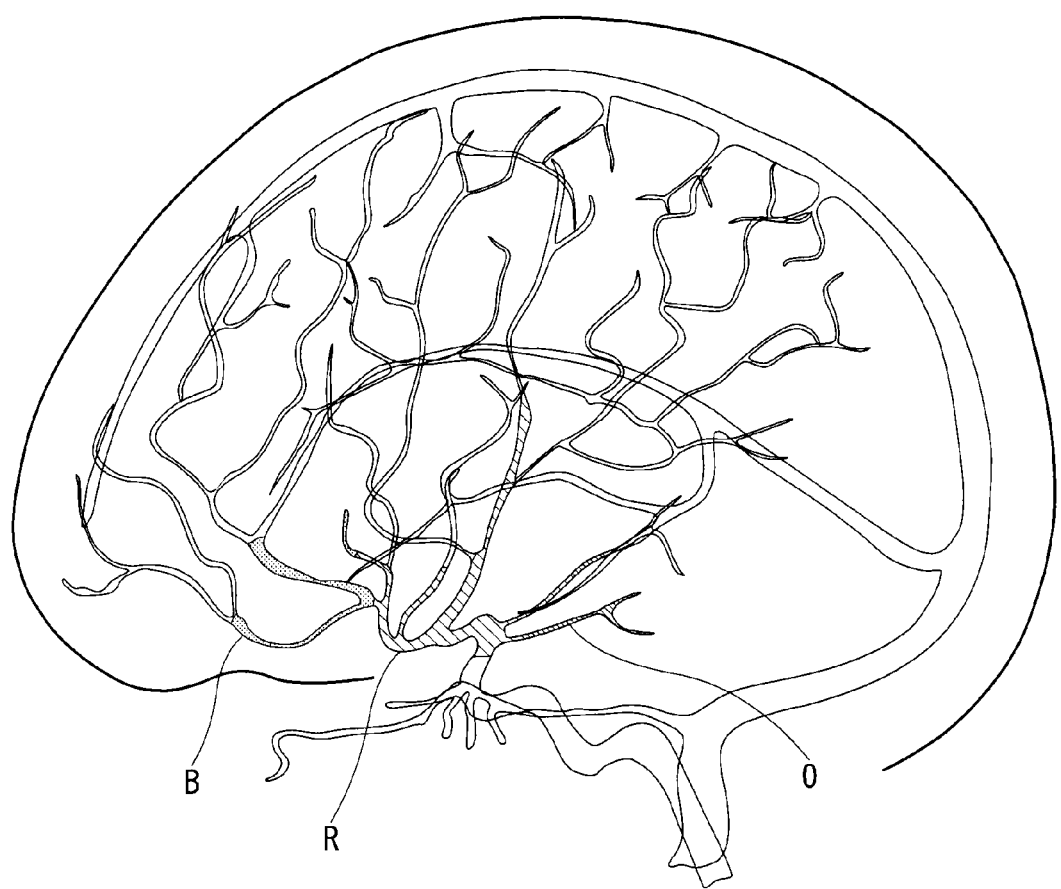
FIG. 15 is a diagram showing an example of a 3D image based on third volume data.

FIG. 15 is a diagram showing an example of the 3D image based on the third volume data. FIG. 15 shows a variation example of FIG. 6.

FIG. 15 shows the 3D image based on the third volume data generated by converting the voxel values showing the head blood vessel shown in FIG. 14 into the voxel values for representing the colors, or three hues (blue B, red R, orange O). The 3D image shown in FIG. 15 allows the operator to visually identify the entire three-dimensionally distributed head vascular morphological information and the brain function information at the same time with no 3D image turning operation.

The displayed 3D image shown in FIG. 15 allows both the head vascular morphological information and the brain function information to be represented using the head vascular morphological shape. Unlike the conventional case, the operator is not required to perform the turning operation for the 3D image for viewing the rear side of the 3D image. The operator can easily grasp the head vascular morphological information and the brain function information.

At least one of embodiments explained in the above can provide information corresponding to a position spatially different from a position of an object to the operator. Furthermore, at least one of embodiments explained in the above can omit the turning operation (turning operation for the direction of line of sight) for the 3D image by the operator for exhaustively identifying the object and the information corresponding to the position spatially different from the position of the object. Consequently, the operational load on the operator can be reduced.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An image processing apparatus, comprising
processing circuitry configured to
obtain first volume data showing a morphological shape of a coronary artery supplying nutrition to a heart and second volume data showing cardiac function information, or obtain first volume data showing a morphological shape of a head blood vessel and second volume data showing brain function information, and
provide luminance information from the second volume data at a position of the coronary artery or the head blood vessel in the first volume data.

2. The image processing apparatus according to claim 1, wherein the processing circuitry is further configured to obtain the first volume data, which shows the morphological shape of the coronary artery and the second volume data, which shows the cardiac function.

3. The image processing apparatus according to claim 1, wherein
the processing circuitry is further configured to convert luminance information at the position of the coronary artery into the luminance information obtained from the second volume data.

4. The image processing apparatus according to claim 2, wherein the processing circuitry is further configured to:
associate the cardiac function information in the second volume data with the coronary artery in the first volume data; and
provide the cardiac function information associated with the coronary artery at the position of the coronary artery.

5. The image processing apparatus according to claim 4, wherein the processing circuitry is further configured to:

determine regions in the second volume data for respective voxels showing the coronary artery in the first volume data; and associate, with the voxels, pieces of the cardiac function information in the regions determined for the respective voxels.

6. The image processing apparatus according to claim 5, wherein the processing circuitry is further configured to:
align the first volume data and the second volume data with each other; and
determine the regions in the second volume data for the respective voxels showing the coronary artery in the first volume data after alignment according to distances from the second volume data after alignment for the voxels showing the coronary artery.

7. The image processing apparatus according to claim 6, wherein the processing circuitry is further configured to:
determine voxels showing a centerline of the coronary artery as respective voxels concerned among the voxels in the second volume data after the alignment;
associate pieces of the cardiac function information in the determined voxels with the coronary artery corresponding to the respective voxels showing the centerline of the coronary artery; and
generate third volume data to which the associated pieces of cardiac function information are provided, at the position of the coronary artery.

8. The image processing apparatus according to claim 6, wherein the processing circuitry is further configured to:
determine multiple voxels within a certain distance from the respective voxels showing a centerline of the coronary artery among the voxels in the second volume data after the alignment;
associate an average value of pieces of the cardiac function information on the determined multiple voxels with the coronary artery corresponding to the voxels showing the centerline of the coronary artery; and
generate third volume data to which the associated pieces of cardiac function information is provided, at the position of the coronary artery.

9. The image processing apparatus according to claim 4, wherein the processing circuitry is further configured to:
determine regions in surface data that is the second volume data for respective voxels showing the coronary artery from the surface data; and
associate the cardiac function information in the regions determined for the respective voxels with the respective voxels.

10. The image processing apparatus according to claim 4, wherein the processing circuitry is further configured to associate the cardiac function information in the second volume data that has a substantially same cardiac time phase as a cardiac time phase of the first volume data with the coronary artery in the first volume data.

11. The image processing apparatus according to claim 4, wherein the processing circuitry is further configured to cause a display to display third volume data to which the associated cardiac function information is provided, as a 3D image or a sectional image, at the position of the coronary artery.

12. The image processing apparatus according to claim 4, wherein the cardiac function information is function information on a cardiac wall.

13. The image processing apparatus according to claim 12, wherein the cardiac function information includes numeric value information, or attribute information on color assigned based on the numeric value information.

14. A medical image diagnostic apparatus, comprising:
a scanner imaging a heart to generate one of first volume data showing a morphological shape of a coronary artery supplying nutrition to the heart and second volume data showing cardiac function information, or taking an imaging of a head to generate one of first volume data showing a morphological shape of a head blood vessel and second volume data showing brain function information; and
processing circuitry configured to obtain other data between the first volume data and the second volume data, and
provide luminance information from the second volume data at a position of the coronary artery or the head blood vessel in the first volume data.

15. The medical image diagnostic apparatus according to claim 14, wherein
the processing circuitry is further configured to obtain the first volume data, which shows the morphological shape of the coronary artery and the second volume data, which shows the cardiac function information.

16. The medical image diagnostic apparatus according to claim 15, wherein the processing circuitry is further configured to convert luminance information at the position of the coronary artery into the luminance information of the second volume data.

17. The medical image diagnostic apparatus according to claim 15, wherein the processing circuitry is further configured to:
associate the cardiac function information in the second volume data with the coronary artery in the first volume data; and
provide the cardiac function information associated with the coronary artery at a position of the coronary artery.

18. An image processing method, comprising:
obtaining first volume data showing a morphological shape of a coronary artery supplying nutrition to a heart and second volume data showing cardiac function information from a memory, or obtaining first volume data showing a morphological shape of a head blood vessel and second volume data showing brain function information;
providing luminance information from the second volume data at a position of the coronary artery or the head blood vessel in the first volume data to generate third volume data; and
displaying the third volume data as an image to a display.

19. The image processing method according to claim 18, further comprising:
obtaining the first volume data, which shows the morphological shape of the coronary artery and the second volume data, which shows the cardiac function information.

20. The image processing method according to claim 19, further comprising:
converting luminance information at the position of the coronary artery into the luminance information of the second volume data.

* * * * *